United States Patent [19]

Grosser et al.

[11] B 3,999,944

[45] Dec. 28, 1976

[54] DETECTION OF BREAST CANCER

[75] Inventors: Norman Grosser, Montreal; David Marshall Parks Thomson, Mount Royal, both of Canada

[73] Assignee: Hoffmann-La Roche Inc., Nutley, N.J.

[22] Filed: Feb. 28, 1975

[21] Appl. No.: 554,039

[44] Published under the second Trial Voluntary Protest Program on February 24, 1976 as document No. B 554,039.

[52] U.S. Cl. .............................. 23/230 B; 424/12
[51] Int. Cl.² ...................................... G01N 33/16
[58] Field of Search .................... 23/230 B; 424/12

[56] References Cited

UNITED STATES PATENTS

| 3,594,466 | 7/1971 | Guffroy | 424/12 |
| 3,663,684 | 5/1972 | Freedman | 424/12 X |
| 3,840,655 | 10/1974 | Lerner | 424/12 |
| 3,852,415 | 12/1974 | Vandervoorde | 424/12 X |
| 3,867,363 | 2/1975 | Hansen | 424/12 X |

OTHER PUBLICATIONS

Chemical Abstracts, 77:99494p (1972).

*Primary Examiner*—Joseph Scovronek
*Assistant Examiner*—Sidney Marantz
*Attorney, Agent, or Firm*—Samuel L. Welt; Bernard S. Leon; Gerald S. Rosen

[57] ABSTRACT

The detection of breast cancer in humans by evaluating antigen induced leukocyte adherence inhibition caused by tumor specific cell mediated immunity by incubating a measured amount of a patients blood leukocytes with aqueous basic extracts of human breast tumor, then determining whether the leukocyte adherence inhibition measured by the non-adherence index as compared to a control of a non-specific antigen is high, indicating the presence of breast cancer, or low, indicating the absence of breast cancer.

4 Claims, No Drawings

DETECTION OF BREAST CANCER

BACKGROUND OF THE INVENTION

Cell mediated tumor immunity has been demonstrated in experiments with transplanted tumors in mice and rats. For example, Halliday et al, Int. J. Cancer, Vol. 9, pages 477–483 (1972) established a simple assay of cell mediated immunity called Leukocyte Adherence Inhibition. This assay was based on the findings that the adherence of peritoneal leukocytes to glass is specifically inhibited by the addition of tumor extracts if the peritoneal leukocytes are obtained from mice which have been presensitized against the specific tumor. Holan et al., Cellular Immunology, Vol. 13, pages 107–116 (1974), using transplanted tumors in rats, mice and guinea pigs also demonstrated the same phenomenon with macrophage cells. There has been much research in attempts to utilize immunological principles for the detection and possible cure for various human cancers. While success has been met in animal models having transplanted tumors, immunological methods developed for the detection of breast cancers have not been successful for mass screening. While it has been generally known that an immunological defense mechanism exists in the early stages of malignant diseases, while such defense mechanism has been demonstrated with breast cancer in humans with macrophage migration inhibition and by interdermal injections of breast antigens which show a delayed hypersensitivity response, such assays are unsuitable for large scale screening.

In recent years a great many studies have been made in the medical diagnostics field to achieve detection of breast cancer in humans, however, no blood tests have been developed which can be used in mass screening programs for breast cancer detection. The diagnostic tests available to the clinician are based on visual observation of cells, x-rays, or thermography. These tests, however, are time consuming, complex and subjective. Ideally, a desirable test for human breast carcinoma would be a blood test which is simple, specific and reproducible and which detects the disease at a sufficiently early stage so that the disease is still curable.

DESCRIPTION OF THE INVENTION

We have discovered that the product of the immunological defense mechanism of the human body to breast cancer can be detected at a stage of the disease which is sufficiently early so the disease is still curable. The method used to detect the product of the immunological defense mechanism is a blood test which is simple to perform, is specific to breast cancer and gives reproducible results. As used herein, "breast cancer" means carcinomas of the breast of humans. Carcinomas include adenocarcinoma.

The process of this invention involves collecting the leukocytes from heparinized venous blood of the patient, then suspending a measured amount of the leukocytes in a buffered solution followed by mixing the leukocytes with extracts of breast cancer tumors, and using as a control extracts of normal breast tissue, or extracts of other tissues or malignant tumors not being detected. After suitable incubation procedures, the number of cells in each case not adhering to the sides of the test tube are counted and the leukocyte adherence inhibition is measured as the non-adherence index (NAI). This determines the presence or absence of breast cancer.

The Non-Adherence Index is calculated according to the following formula:

$$\frac{\% \text{ non-adherent cells in presence of specific antigen} - \% \text{ non-adherent cells in presence of non-specific antigens}}{\% \text{ non-adherent cells in presence of non-specific antigen}} \times 100$$

The leukocytes are collected and counted by conventional methods. The heparinized blood sample is incubated at about 37°C. for about one hour and the plasma fraction is collected. The plasma fraction is rich in leukocytes. The leukocytes are separated by centrifugation and suspended in an isotonic buffer. Any erythrocytes remaining are lysed from the leukocyte suspension. The leukocytes are then separated by centrifugation and suspended in an appropriate aqueous medium at a cell concentration of $1 \times 10^7$/ml.

The tumor extracts are made by homogenizing the tumor samples (or normal tissue samples), in an ice-cold buffered saline at pH about 7.3, centrifuging the homogenate and collecting the resulting supernatant. The buffer used is preferably a phosphate buffered saline (PBS). It is necessary to use a basic pH since acid pH will destroy the antigenic activity. In order to use in the assay, the extracts are diluted with an appropriate aqueous medium, preferably Medium 199 (Microbiological Associates, Bethesda, Md.). The optimum dilution for use in the assay is established for each extract by determining the concentration of tumor antigen which produces the largest increment between the specific and non-specific inhibition of leukocyte adherence.

The breast tumor extract is the antigenic material which gives rise to the cell mediated immunity. For purposes of illustrating this invention, breast adenocarcinoma extracts are used. The antigens which are suitable for use as the non-specific controls are extracts of normal breast tissue, melanoma tumor, adenocarcinoma of the bowel, ovary and bladder and lung cancer.

The assay is carried out by mixing aliquots of a small amount of a blood leukocyte suspension containing about $1 \times 10^7$ leukocytes/ml. with separate small amounts of buffer, breast tumor antigen, or unrelated antigen in separate glass containers. Each mixture is then brought to a predetermined volume. Each mixture is then incubated in the glass container which is placed so that the contents cover at least three-fourths of the inner surfaces of the container. The incubation is carried out at about 37°C. for a sufficient time to complete the reaction, if any, under a humidified atmosphere of 5% $CO_2$-air. When the incubation is completed, the contents are agitated and the number of non-adherent cells are counted.

The aliquots of leukocyte suspension are conveniently very small, usually about 0.1 ml. The concentration of leukocytes is such that counting of the cells gives a meaningful result and the reaction with the antigen material can be readily assayed. The buffer used for dilution is Medium 199 which has a pH of 7.2–7.4.

The amount of antigen extract used is conveniently about 0.1 ml. of the diluted extract. The extract is diluted generally with Medium 199. The amount of dilution of the concentrated antigen extract on a volume basis can be between 1 part antigen extract per 4 to 16 parts of diluent. Preferably a 1 to 4 dilution is used.

The final volume of the test mixture of leukocytes and antigen is conveniently about 0.5 ml. The diluent used to achieve this volume is Medium 199.

Suitable glass containers used are any convenient size and shape. For convenience of use and availability, 20 ml. Pyrex test tubes are preferred. The incubation is carried out with the test tubes in a horizontal position in a holder which prevents their movement. This is critical since movement during incubation can adversely affect the test results. The incubation is carried out preferably for about two hours. Longer times can be used but do not increase the accuracy of the assay or the completeness of the reaction. Shorter times can also be used but are not optimum. Thus incubation times of from about 1 to 3 hours are operable.

The non-adherent cells are counted in any convenient manner, for example, by the use of a hemocytometer. It has been found according to the process used in this invention that the response of the leukocytes of a patient to breast cancer tumor extracts does not depend upon the source of the extract. Extracts from the patient who is being tested or extracts from other patient's breast cancers give equivalent results. This indicates that the leukocytes of a patient with breast cancer exhibit cell mediated immunity which is specific to all breast cancers of the same type and is not affected by the source of the breast cancer antigen.

The following Examples illustrate the invention.

EXAMPLE 1

Tumor Extracts

Breast tumor samples were received at operation and placed in a sterile container. Fat and fibrous tissue were dissected away and the specimen was finely minced with sharp scissors in ice-cold phosphate-buffered saline (PBS), pH 7.3. The resulting material was homogenized for 10–15 minutes in four volumes of PBS at 40,000 rpm in a VirTis 45 homogenizer. The homogenate was centrifuged at 20,000 × gravity for 30 minutes and the supernatants were collected and stored at −40°C. in small aliquots. Extracts of normal breast tissue, malignant melanoma and other tumors were prepared in an identical manner. These extracts were used as the controls for the process of this invention. For use in the assay, the extracts were thawed and diluted to 1:4 volume with Medium 199. Medium 199 is marketed by Microbiological Associates, Bethesda, Maryland and is composed of

| Components | mg./liter |
| --- | --- |
| Amino Acids | |
| L-Alanine | 25.0 |
| L-Aginine HCl | 70.0 |
| L-Aspartic Acid | 30.0 |
| L-cysteine HCl | 0.1 |
| L-Cystine | 20.0 |
| L-Glutamic Acid | 67.0 |
| L-Glutamine | 100.0 |
| Glycine | 50.0 |
| L-Histidine HCl-H$_2$O | 22.0 |
| Hydroxy-L-proline | 10.0 |
| L-Isoleucine | 20.0 |
| L-Leucine | 60.0 |
| L-Lysine HCl | 70.0 |
| L-Methionine | 15.0 |
| L-Phenylalanine | 25.0 |
| L-Proline | 40.0 |

-continued

| Components | mg./liter |
| --- | --- |
| L-Serine | 25.0 |
| L-Threonine | 30.0 |
| L-Tryptophan | 10.0 |
| L-Tyrosine | 40.0 |
| L-Valine | 25.0 |
| Vitamins | |
| P-Aminobenzoic Acid | 0.050 |
| Ascorbic Acid | 0.050 |
| D-Biotin | 0.010 |
| Calciferol | 0.100 |
| D-Ca-Pantothenate | 0.010 |
| Cholesterol | 0.200 |
| Choline Chloride | 0.500 |
| Folic Acid | 0.010 |
| i-Inositol | 0.050 |
| Menadione | 0.010 |
| Nicotinamide | 0.025 |
| Nicotinic Acid | 0.025 |
| Pyridoxal HCl | 0.025 |
| Pyridoxine HCl | 0.025 |
| Riboflavin | 0.010 |
| Thiamine HCl | 0.010 |
| DL-α-Tocopherolphosphate (Na$_2$) | 0.010 |
| Tween 80* | 5.000 |
| Vitamin A.Acetate | 0.140 |
| Other Components | |
| Adenine HCl.2H$_2$O | 12.10 |
| Adenosine-5′-Monophosphoric acid, dihydrate (AMP) (Muscle Adenylic Acid) | 0.20 |
| Adenosine-5′-Triphosphate disodium, tetrahydrate (ATP) | 1.08 |
| Deoxyribose | 0.50 |
| Dextrose | 1000.00 |
| Glutathione (Reduced) | 0.05 |
| Guanine HCl.H$_2$O | 0.33 |
| Hypoxanthine | 0.30 |
| Phenol Red | 20.00 |
| Ribose | 0.50 |
| Sodium Acetate.3H$_2$O | 83.00 |
| Thymine | 0.30 |
| Uracil | 0.30 |
| Xanthine | 0.34 |
| Inorganic Salts | |
| CaCl$_2$.2H$_2$O | 186.0 |
| Fe(NO$_3$)$_3$.9H$_2$O | 0.7 |
| KCl | 400.0 |
| KH$_2$PO$_4$ | 60.0 |
| MgSO$_4$.7H$_2$O | 200.0 |
| NaCl | 8000.0 |
| NaHCO$_3$ | 1400.0 |
| Na$_2$HPO$_4$.7H$_2$O | 90.0 |
| Vialed at pH 7.2 to 7.4 | |

*Trademark of Atlas Powder Company - Polyoxyethylene (20) sorbitan monooleate

EXAMPLE 2

Preparation of the Leukocyte Reagent

Blood was taken from patients with breast cancer and control subjects and immediately stored at 4°C. After retraction of the clot overnight, the serum was separated and stored at −40°C. These blood samples were heparinized blood samples obtained from patients with adenocarcinoma of the breast and controls with benign breast disease and a variety of non-malignant diseases or unrelated malignancies. The diagnosis of breast cancer in the so designated patients was confirmed histologically. The clinical diagnosis of all apparently benign breast lesions was confirmed by histological examinations of the surgical specimen. 20 Ml. samples of the heparinized blood, i.e., venous blood, was placed vertically in a glass universal bottle at 37°C. for 1 hour. The resulting leukocyte rich plasma fraction was aspirated and centrifuged at 200 × gravity for 15 minutes. The plasma was removed and discarded. The remaining cell button was suspended in an ice cold isotonic Tris-buffered ammonium chloride solution by repeated pipetting and left for 15 minutes at 4°C. in order to lyse any remaining erythrocytes. This procedure was terminated by the addition of 3 ml. of Medium 199 and the cells were centrifuged at 200 × gravity for 15 minutes. The resulting supernatant was removed and discarded and the remaining cells were then washed twice in 20 volumes of Medium 199. Aliquots of the leukocytes were made at a concentration of 1 × 10$^7$ cells per ml. using Medium 199 as the diluent.

EXAMPLE 3

LAI Assay

Aliquots of 0.1 ml. of blood leukocytes suspensions containing 1 × 10$^7$ cells per ml. were placed in glass test tubes. Added to these leukocytes were 0.1 ml. of extracts of either breast tissue or other unrelated tumor cell derived preparations or 0.1 ml. of extracts of cancer tumors from the breast. Various concentrations of tumor extracts were used to determine the optimum concentration. The mixture of leukocytes and test cells were brought to a final volume of 0.5 ml. by the addition of Medium 199. The mixture was then stirred and the tubes were put in a horizontal position so that the contents of the tubes covered three-fourths of the surface of the tubes. The horizontal tubes were then incubated at 37°C. in a humidified atmosphere of 5% $CO_2$-air for 2 hours. The tubes were not disturbed or moved during the incubation period. After the incubation the tubes were placed vertically and the contents were agitated with a pasteur pipette. The number of non-adherent cells/ml. was counted in a hemocytometer. All assays were done in triplicate. The results expressed as the non-adherence index (NAI) is shown in the following table:

Table 1

ANTIGEN MEDIATED LEUKOCYTE ADHERENCE INHIBITION TO GLASS BY BREAST TUMOR EXTRACT

| Diagnosis in Clinic | % Non-Adherent Cells in Presence of | | | Non-Adherence Index[a] |
|---|---|---|---|---|
| | Breast Tumor Antigen | Melanoma Antigen | No Antigen | |
| Breast Ca | 48 ± 3.5 | 26 ± 5.0 | 8 ± 2.0 | 84 |
| Breast Ca | 50 ± 3.0 | 31 ± 3.0 | 11 ± 1.5 | 61 |
| Breast Ca | 40 ± 2.8 | 22 ± 5.2 | 3 ± 1.0 | 82 |
| Breast Ca | 56 ± 4.5 | 36 ± 4.5 | 16 ± 2.5 | 56 |
| Fibroadenoma of Breast | 26 ± 3.5 | 28 ± 3.5 | 10 ± 2.5 | 09 |
| Fibrocystic Breast Dis. | 40 ± 3.5 | 35 ± 5.0 | 5 ± 2.1 | 13 |
| Melanoma | 35 ± 6.0 | 70 ± 4.5 | 10 ± 2.8 | −50 |
| Melanoma | 34 ± 4.0 | 63 ± 4.5 | 8 ± 1.8 | −44 |

[a]Non-adherence index using breast cancer antigen as specific antigen and melanoma as non-specific antigen.

$$NAI = 100 \times \frac{\% \text{ Non-adherent cells in presence of breast cancer antigen} - \% \text{ Non adherent cells in presence of unrelated antigen}}{\% \text{ Non-adherent cells in presence of unrelated antigen}}$$

The results indicate that the patients with breast cancer have a significantly higher NAI when compared to other patients.

When blood leukocytes from breast cancer patients or control subjects were incubated in glass tubes without added antigen for 2 hours, about 10 percent non-adherent cells were found. The addition of any tumor extract or normal breat tissue extract to non-sensitized blood leukocytes inhibited adherence of 15–40 percent of the leukocytes. Incubation of blood leukocytes from patients with breast cancer, with breast tumor extracts, caused a 40–65 percent non-adherence of leukocytes to glass, whereas incubating the same cells with normal breast tissue, melanoma extract or other unrelated tumor extracts produced a 15–40 percent non-adherence of leukocytes. Leukocyte adherence-inhibition was the same when the breast carcinoma patient's leukocytes were exposed to extracts of their own tumor as when the extract was from breast carcinoma of another individual.

In order to achieve the optimum assay conditions, that is, the maximum specific inhibition of leukocyte adherence with the least non-specific inhibition, the antigen extracts were tested at different concentrations with leukocytes from patients with malignant melanoma, breast cancer, and control subject. As shown in Table 2, the NAI falls with increasing dilutions. In this instance, however, a dilution of one-fourth of the breast cancer extract and melanoma extract gave a high NAI value for the patient with breast cancer and a low NAI to breast cancer for both the control and patient with malignant melanoma. Therefore, for the purpose of this invention, a dilution of one-fourth of the antigen, that is, one part antigen extract to 4 parts of diluent are preferred. Good results are obtained, however, when the dilution is as high as 1:16.

Table 2

EFFECT OF DILUTING ANTIGEN ON LEUKOCYTE ADHERENCE INHIBITION

| Diagnosis of Leukocyte Donor | Dilution of Antigens | Non-Adherence Index to Breast Cancer[a] |
|---|---|---|
| Cancer of Breast | 1:4 | 300 |
| | 1:8 | 240 |
| | 1:16 | 220 |
| Melanoma | 1:4 | −35 |
| | 1:8 | −20 |
| | 1:16 | −18 |
| Cholelithiasis | 1:4 | −3.0 |
| | 1:8 | −2.5 |
| | 1:16 | −3.2 |

[a]Non-adherence index using breast cancer antigen as specific antigen and melanoma as non-specific antigen.

The results shown in Tables 3 and 4 indicate that significant inhibition of leukocyte adherence to glass occurred with breast cancer extracts with cells from 40 of 47 breast cancer patients. The breast cancer patients showed a mean NAI of 58 and 189 to the breast cancer extract when the non-specific antigens were melanoma and normal breast tissue, respectively. There is a striking difference in the NAI between breast cancer patients who have clinically localized disease to breast or breast and lymph nodes compared with individuals with cancer spread to multiple organs. Six patients showed a NAI below the arbitrary level of 18 when the melanoma extract was employed as a control. Three of the six patients had disseminated disease, one patient had axillary node involvement but no clinical evidence of metastasis and the remaining two patients had small breast lumps which histologically showed invasive adenocarcinoma. This is apparent from Table 3. When normal breast tissue was used as the non-specific control antigen, only one breast cancer patient had a NAI below the arbitrary level of 60. This is shown in Table 4. This patient had disseminated cancer.

Thirty-two controls had no clinical evidence of breast cancer. In general, the controls failed to demonstrate breast tumor antigen-induced inhibition of leukocyte glass adherence as a group and as individuals. The mean Non-Adherence Index of the breast cancer patients is significantly different from the corresponding control group (P<.001).

Tumor antigen-induced inhibition of leukocyte adherence to glass in patients with breast cancer and controls. The Non-Adherence Index was calculated using breast cancer antigen as specific antigen and melanoma extract as unrelated antigen. NAI = % non-adherent cells with specific antigen − % non-adherent cells with non-specific antigen divided by % non-adherent cells with non-specific antigen. A NAI of 18 or greater was considered significant. The breast cancer group consisted of 23 patients with active disease. The control group consisted of 19 patients with variety of diagnosis, 7 of whom had histologically proven benign breast disease. The mean NAI of the breast cancer Table 3

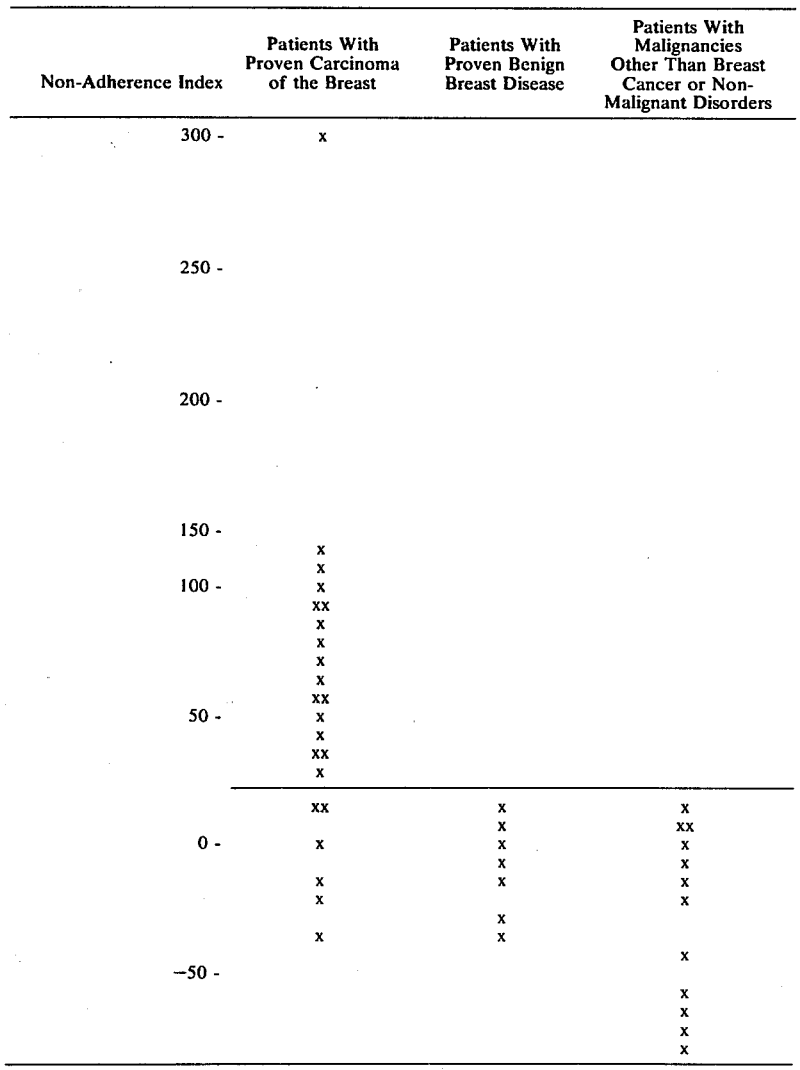

group of 58 is significantly different from the control group (−18). (P<.001 by unpaired t-test).

Table 4

| NON-ADHERENCE INDEX | Patients With Proven Carcinoma of the Breast | Patients With Proven Benign Breast Disease | Patients With Malignancies Other Than Breast Cancer or Non-Malignant Disorders |
| --- | --- | --- | --- |
| 500 - | | | |

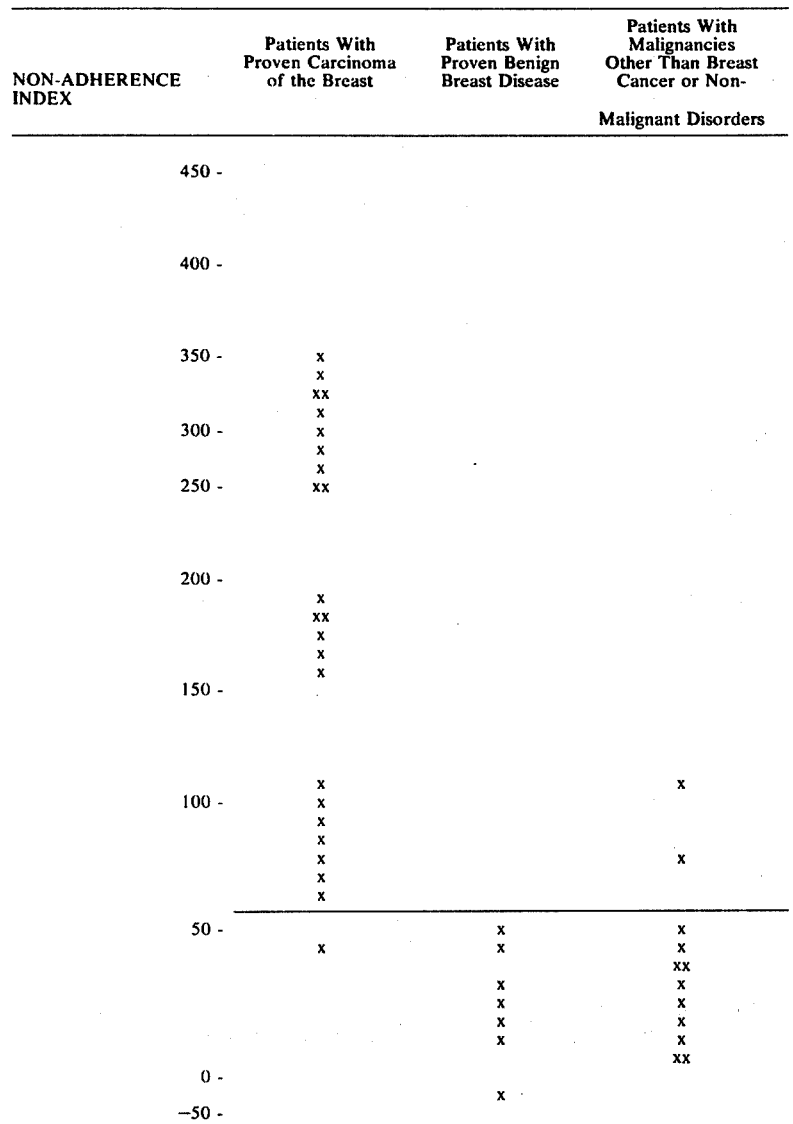

Tumor antigen induced inhibition of leukocyte adherence to glass in patients with breast cancer and controls. The Non-Adherence Index was calculated using breast cancer as specific antigen and normal breast tissue as unrelated antigen. A NAI of 60 and greater was considered significant. The breast cancer group consisted of 24 patients with active disease. The control consisted of 20 patients, 7 of whom were the same patients with the benign breast disease. The mean NAI of the breast cancer group is 158 and is significatnly different from the controup, 30. (P<.001 by unpaired t-test).

Other tumor extracts have been employed as the non-specific antigens. The results have been exactly similar to those obtained with the melanoma extract as the non-specific control. No evidence of cross-reaction has been observed.

We claim:

1. A method for detecting the presence of breast cancer in humans which comprises incubating a measured amount of a patient's blood leukocytes with aqueous basic extracts of human breast tumor, then determining the leukocytes non-adherence index by comparison to a non-specific antigen control, and concluding that breast cancer is present if the non-adherence index of the patient being tested is higher than the control non-adherence index.

2. The method of claim 1 wherein the breast tumor extract is from a breast tumor of the patient being tested.

3. The method of claim 2 wherein the breast tumor extract is from a breast tumor of a patient not being tested.

4. The process of claim 1 wherein the breast tumor extract is an aqueous extract at pH 7.3.

* * * * *